United States Patent
Stanfield et al.

(10) Patent No.: US 10,881,430 B2
(45) Date of Patent: Jan. 5, 2021

(54) TISSUE INTERFACE APPARATUS, SYSTEMS, AND METHODS

(71) Applicant: VADovations, Inc., Oklahoma City, OK (US)

(72) Inventors: J. Ryan Stanfield, Sandy, UT (US); James W. Long, Edmond, OK (US); Michael A. Vladovich, Edmon, OK (US)

(73) Assignee: VADovations, Inc., Oklahoma City, OK (US)

( * ) Notice: Subject to any disclaimer, the term of this patent is extended or adjusted under 35 U.S.C. 154(b) by 0 days.

(21) Appl. No.: 16/380,338

(22) Filed: Apr. 10, 2019

(65) Prior Publication Data

US 2019/0314058 A1    Oct. 17, 2019

Related U.S. Application Data

(60) Provisional application No. 62/655,937, filed on Apr. 11, 2018.

(51) Int. Cl.
*A61B 17/34* (2006.01)
*A61B 17/00* (2006.01)

(52) U.S. Cl.
CPC .... *A61B 17/3423* (2013.01); *A61B 17/00234* (2013.01); *A61B 17/3468* (2013.01);
(Continued)

(58) Field of Classification Search
CPC . A61B 17/34; A61B 17/3423; A61B 17/3468; A61B 17/3496; A61B 17/00; A61B 17/00324
See application file for complete search history.

(56) References Cited

U.S. PATENT DOCUMENTS

| | | | |
|---|---|---|---|
| 6,241,743 B1 | 6/2001 | Levin et al. | |
| 6,458,153 B1 * | 10/2002 | Bailey | A61F 2/243 623/1.24 |

(Continued)

FOREIGN PATENT DOCUMENTS

WO    2015173609 A1    11/2015

OTHER PUBLICATIONS

Notification of Transmittal of the International Search Report and the Written Opinion of the International Searching Authority, dated Aug. 2, 2019, PCT/US2019/026761.

*Primary Examiner* — Christopher J Beccia
(74) *Attorney, Agent, or Firm* — Daniel J. Honz; Advent, LLP

(57) ABSTRACT

In an aspect, a device includes a body structure including a core and a sleeve disposed around at least a portion of the core, the core defining a channel through the core extending from a first end of the core to a second end of the core, the sleeve including a flange adjacent the second end of the core; and a deployable portion coupled to the body structure adjacent the first end of the core, the deployable portion having a wired structure transitionable between a retained configuration and a deployed configuration, wherein a top portion of the wired structure extends beyond the first end of the core in a longitudinal direction when the wired structure is in the retained configuration, and wherein first end of the core extends beyond the top portion of the wired structure when the wired structure is in the deployed configuration.

20 Claims, 14 Drawing Sheets

(52) U.S. Cl.
CPC .... *A61B 17/3496* (2013.01); *A61B 2017/348* (2013.01); *A61B 2017/3435* (2013.01); *A61M 2210/125* (2013.01)

(56) References Cited

U.S. PATENT DOCUMENTS

| | | | |
|---|---|---|---|
| 6,468,303 B1 * | 10/2002 | Amplatz | A61B 17/11 623/1.2 |
| 8,246,671 B2 * | 8/2012 | Khairkhahan | A61B 17/0057 623/1.11 |
| 8,795,161 B2 | 8/2014 | Carter | |
| 9,314,556 B2 | 4/2016 | Tuseth | |
| 2004/0249400 A1 | 12/2004 | Vargas et al. | |
| 2012/0143141 A1 * | 6/2012 | Verkaik | A61M 1/10 604/175 |
| 2013/0150654 A1 | 6/2013 | Stanfield et al. | |
| 2014/0046347 A1 * | 2/2014 | Cully | A61B 17/12168 606/151 |
| 2015/0196321 A1 | 7/2015 | Gregory et al. | |
| 2018/0021029 A1 | 1/2018 | Bennett, III | |

* cited by examiner

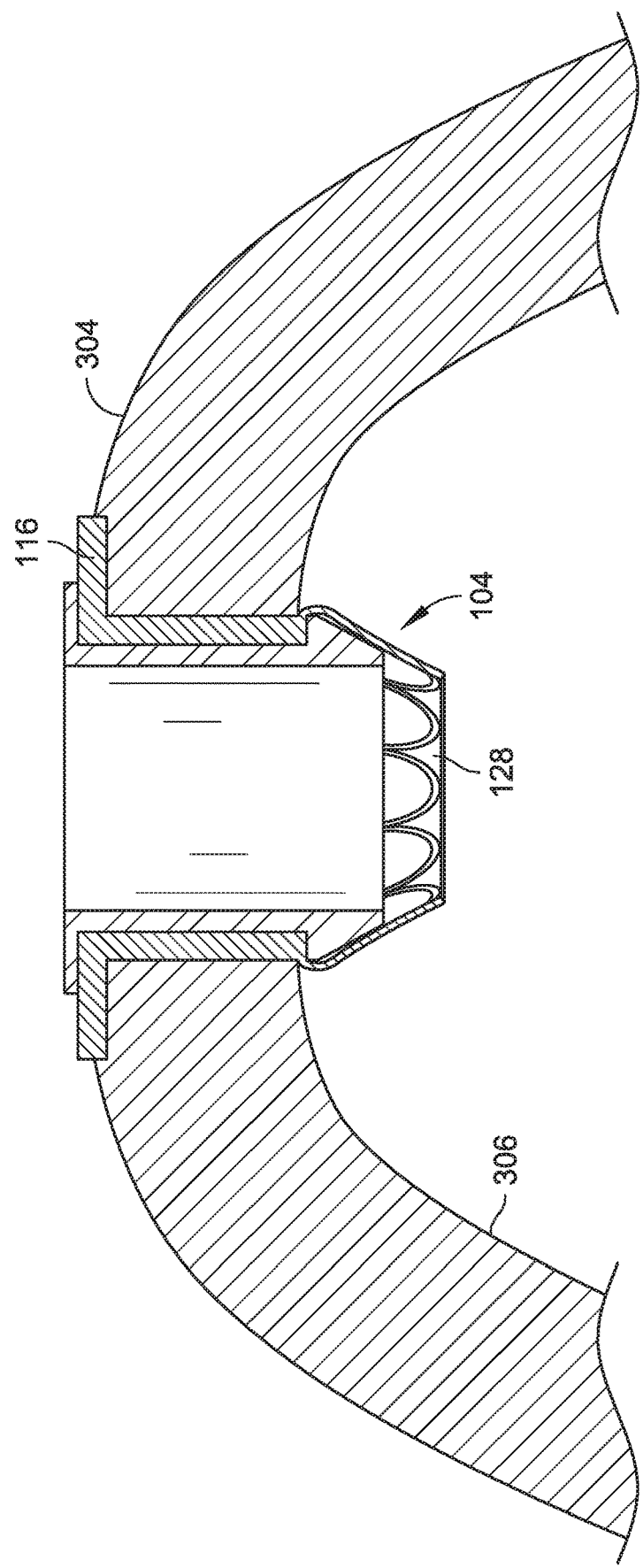

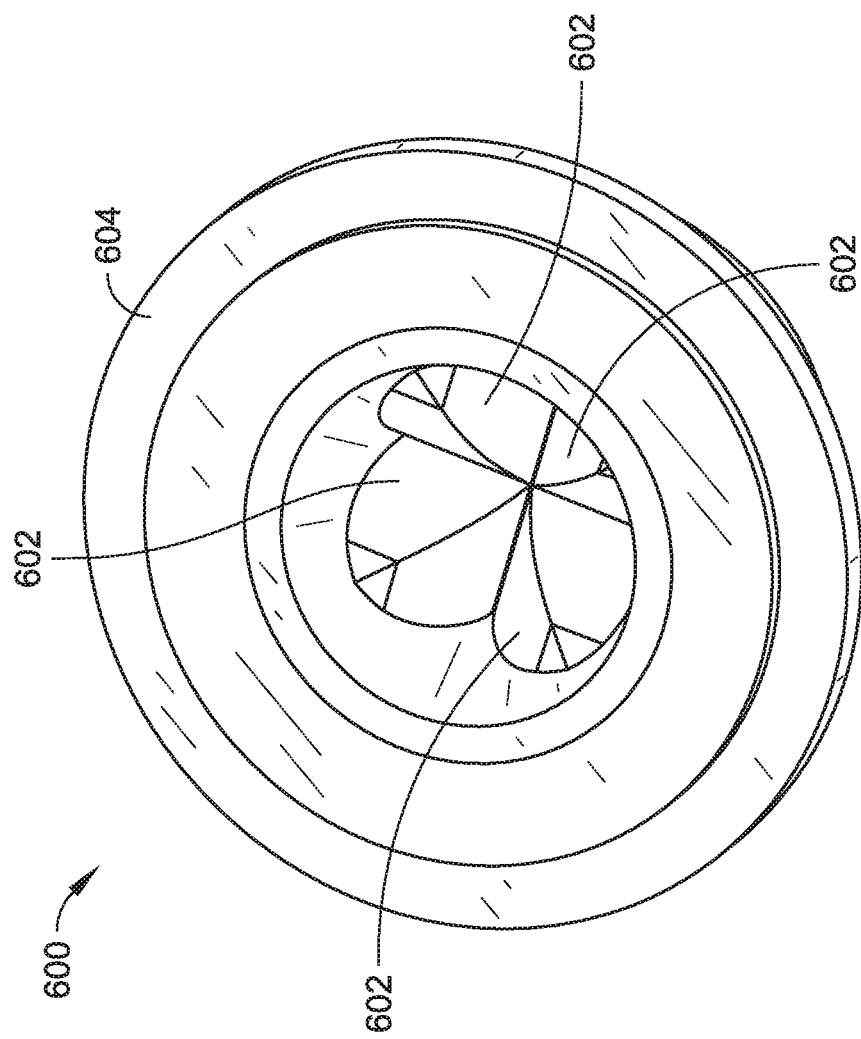

TISSUE INTERFACE APPARATUS, SYSTEMS, AND METHODS

CROSS-REFERENCE TO RELATED APPLICATIONS

The present application claims the benefit under 35 U.S.C. § 119(e) to U.S. Provisional Patent Application Ser. No. 62/655,937, filed Apr. 11, 2018, and titled "TISSUE INTERFACE APPARATUS, SYSTEMS, AND METHODS," which is incorporated herein by reference in its entirety.

BACKGROUND

For many medical procedures, access to an interior cavity of a hollow organ is required. A port or other access point can be used to facilitate access between the interior cavity of an organ and a device, such as a blood pump, ventricular assist device, bypass valve, or other device. However, the interface between rigid or semirigid devices and malleable tissue can pose a risk for leakage of bodily fluid at the interface. Further, the presence of a foreign object on or within the interior cavity can pose a risk of improper ingrowth of tissue, which can block ports or other flow paths, or can fail to provide stable neointima to support and stabilize the object.

SUMMARY

This Summary is provided to introduce a selection of concepts in a simplified form that are further described below in the Detailed Description. This Summary is not intended to identify key and/or essential features of the claimed subject matter. Also, this Summary is not intended to limit the scope of the claimed subject matter in any manner.

Aspects of the disclosure relate to biologic tissue interface devices and systems. In an aspect, a device includes, but is not limited to, a body structure including a core and a sleeve disposed around at least a portion of the core, the core defining a channel through the core extending from a first end of the core to a second end of the core, the sleeve including a flange adjacent the second end of the core; and a deployable portion coupled to the body structure adjacent the first end of the core, the deployable portion having a wired structure transitionable between a retained configuration and a deployed configuration, wherein a top portion of the wired structure extends beyond the first end of the core in a longitudinal direction from the first end of the core to the second end of the core when the wired structure is in the retained configuration, and wherein the first end of the core extends beyond the top portion of the wired structure when the wired structure is in the deployed configuration.

In an aspect, a device includes, but is not limited to, a body structure including a core and a sleeve disposed around at least a portion of the core, the core defining a channel through the core extending from a first end of the core to a second end of the core, the body structure defining a first vertical perimeter extending longitudinally from an interior surface of the core in a direction from the second end of the core to the first end of the core and a second vertical perimeter extending longitudinally from an exterior surface of the body portion in a direction from the second end of the core to the first end of the core, the sleeve including a flange adjacent the second end of the core; and a deployable portion coupled to the body structure adjacent the first end of the core, the deployable portion having a wired structure transitionable between a retained configuration and a deployed configuration, wherein an end portion of the wired structure is held within the first vertical perimeter when the wired structure is in the retained configuration, and wherein the end portion of the wired structure extends beyond the second vertical perimeter in a direction from the channel to the exterior surface of the body portion when the wired structure is in the deployed configuration.

DRAWINGS

The Detailed Description is described with reference to the accompanying figures.

FIG. 3E is a partial cross-sectional view of the biologic tissue interface device of FIG. 3C inserted into the opening in the heart wall with the deployable portion in the retained configuration.

FIG. 6A is an isometric view of a hemostatic valve seal in accordance with example implementations of the present disclosure.

DETAILED DESCRIPTION

Figure 1A:
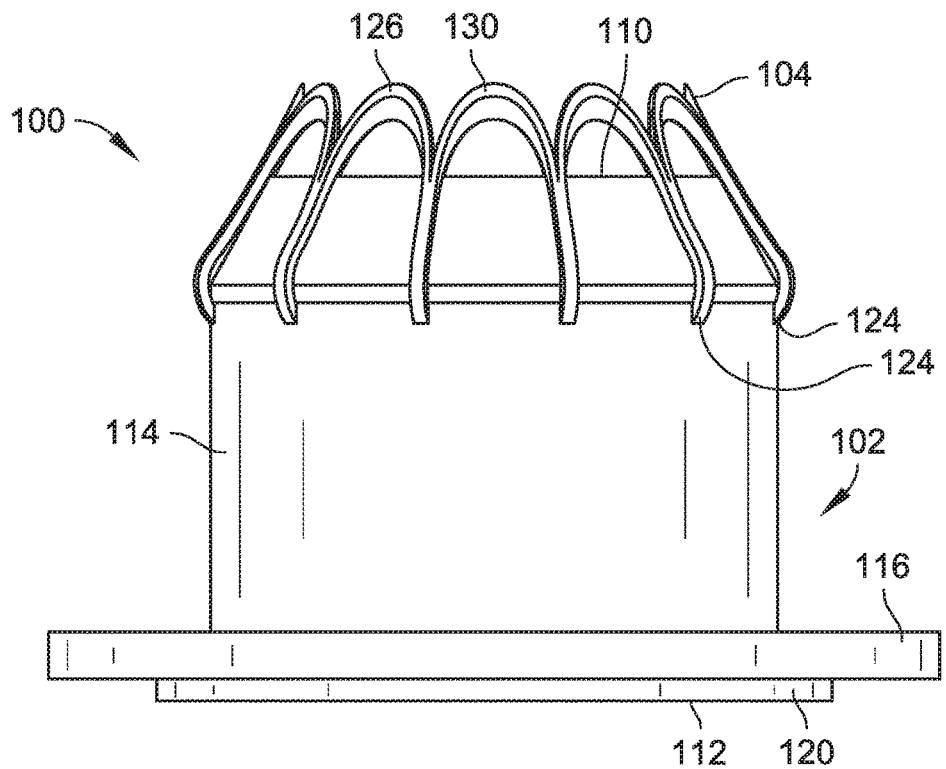
FIG. 1A is a side view of a biologic tissue interface device in accordance with example implementations of the present disclosure.

Aspects of the disclosure are described more fully hereinafter with reference to the accompanying drawings, which form a part hereof, and which show, by way of illustration, example features. The features can, however, be embodied in many different forms and should not be construed as limited to the combinations set forth herein; rather, these combinations are provided so that this disclosure will be thorough and complete, and will fully convey the scope. The following detailed description is, therefore, not to be taken in a limiting sense.

Devices are described herein to provide a stable interface relative to biologic tissue, such as a biological organ, to permit stable tissue ingrowth, and to provide an aperture through the organ wall an interior an interior of the organ without tissue deposition along the aperture. For instance, the devices can permit passage of fluids or other materials between an exterior of an organ and an interior of the organ, support the device with respect to the organ to facilitate coupling with an external device (e.g., pump, conduit, etc.), or combinations thereof, while providing surfaces for stable hyperplasia and neointima formation that permit a smooth transition of exposed substrate in the flow path between native biologic tissue and the device material. Referring to FIGS. 1A through 2B, a device 100 is shown generally including a body portion 102 and a deployable portion 104. The body portion 102 includes a core 106 defining a generally cylindrical channel 108 (shown in FIGS. 2A and 2B) between a first end 110 of the core 106 and a second end 112 of the core 106 distal the first end 110. The body portion 102 also includes a sleeve 114 coupled to the core 106. In implementations, the sleeve 114 includes a flange 116 extending outwardly from the sleeve 114 with respect to the position of the core 106. For example, the sleeve 114 can be coupled between a first flange 118 of the core 106 located adjacent the first end 110 and a second flange 120 of the core 106 located adjacent the second end 112. An exterior surface of the sleeve 114 can facilitate hemostasis when the device 100 is inserted into an opening in native biologic tissue (e.g., by having an external surface 115 of the sleeve 114 in physical contact with the biologic tissue to exert pressure, etc.). The core 106 is formed from a rigid or semi-rigid material having a smooth interior surface 122 defining the channel 108 to limit deposition of native biologic material, to limit ingrowth of native biologic material, or combinations thereof. The channel 108 can be filled with a pump or conduit to control or direct fluid flow through and around the device 100 (e.g., fitted with a right ventricular assist device (RVAD) or a left ventricular assist device (LVAD), bypassing an atrioventricular block (AVB), etc.). The channel 108 alternatively or additionally can be fitted with a plug or other structural impediment (e.g., a valve) to block one or more ends of the channel 108 (e.g., at the second end 112) to provide hemostasis (e.g., before or after insertion of a pump or conduit) or otherwise restrict the flow of fluid through one or more ends of the channel 108. The sleeve 114 is generally formed from, or includes, materials for supporting ingrowth of native biologic material and supporting hemostasis. For example, the sleeve 114 can include, but is not limited to, a fibrous material, a polytetrafluoroethylene (PTFE) felt, polyethylene terephthalate (PET), bovine pericardium, or the like, or combinations thereof.

Figure 3A:
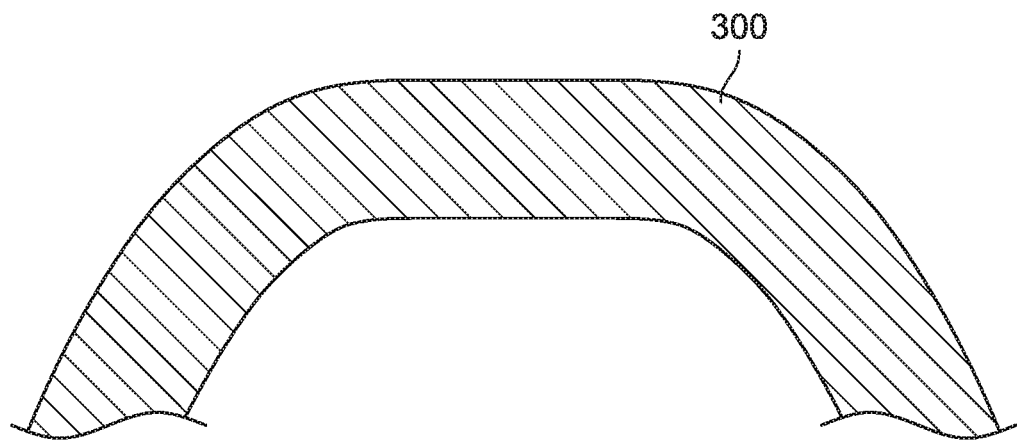
FIG. 3A is a partial cross-sectional view of a heart wall.
Figure 3B:
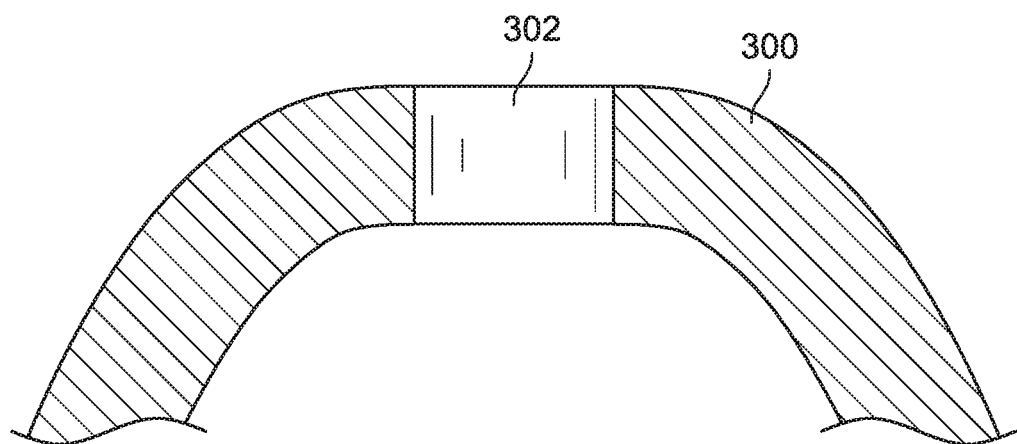
FIG. 3B is a partial cross-section view of the heart wall of FIG. 3A with an opening made therein.
Figure 3C:
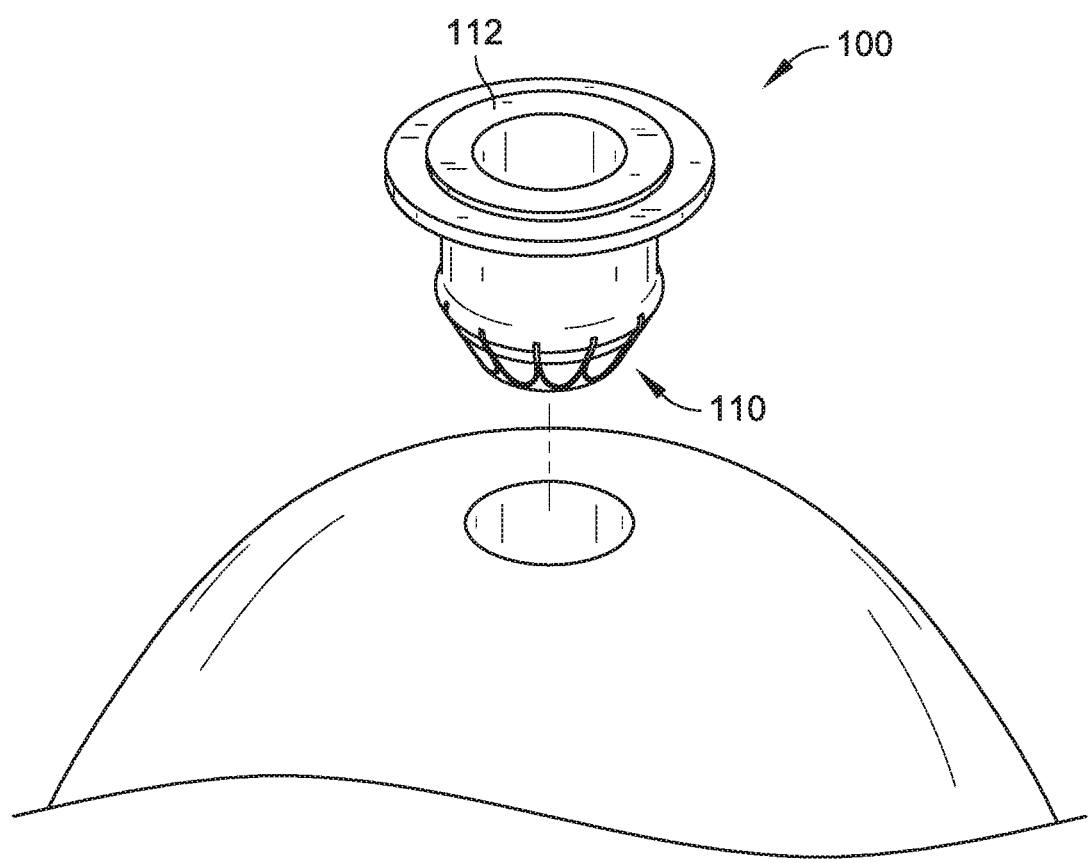
FIG. 3C is a partial isometric view of a biologic tissue interface device being positioned for insertion into the opening in the heart wall of FIG. 3B in accordance with example implementations of the present disclosure.
Figure 3D:
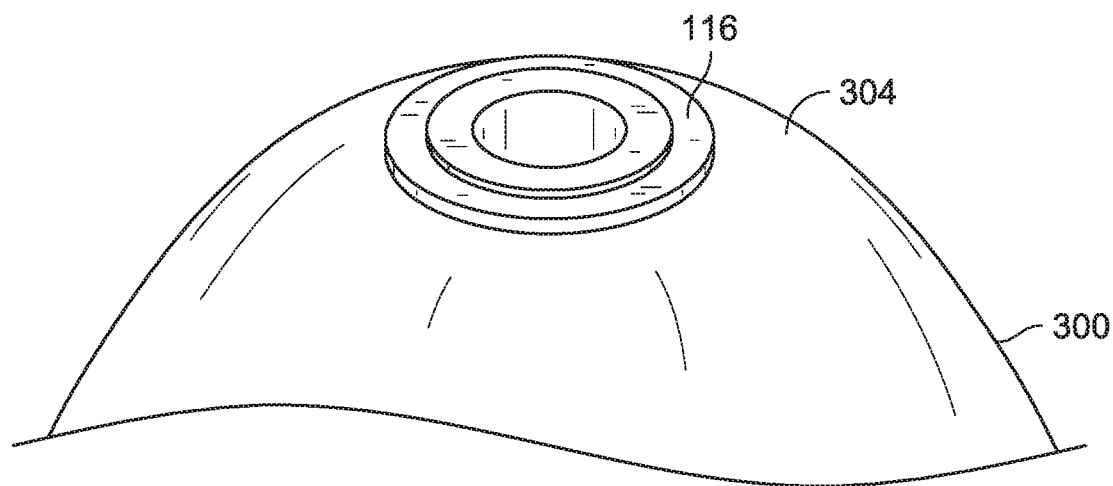
FIG. 3D is a partial isometric view of the biologic tissue interface device of FIG. 3C inserted into the opening in the heart wall.
Figure 3F:
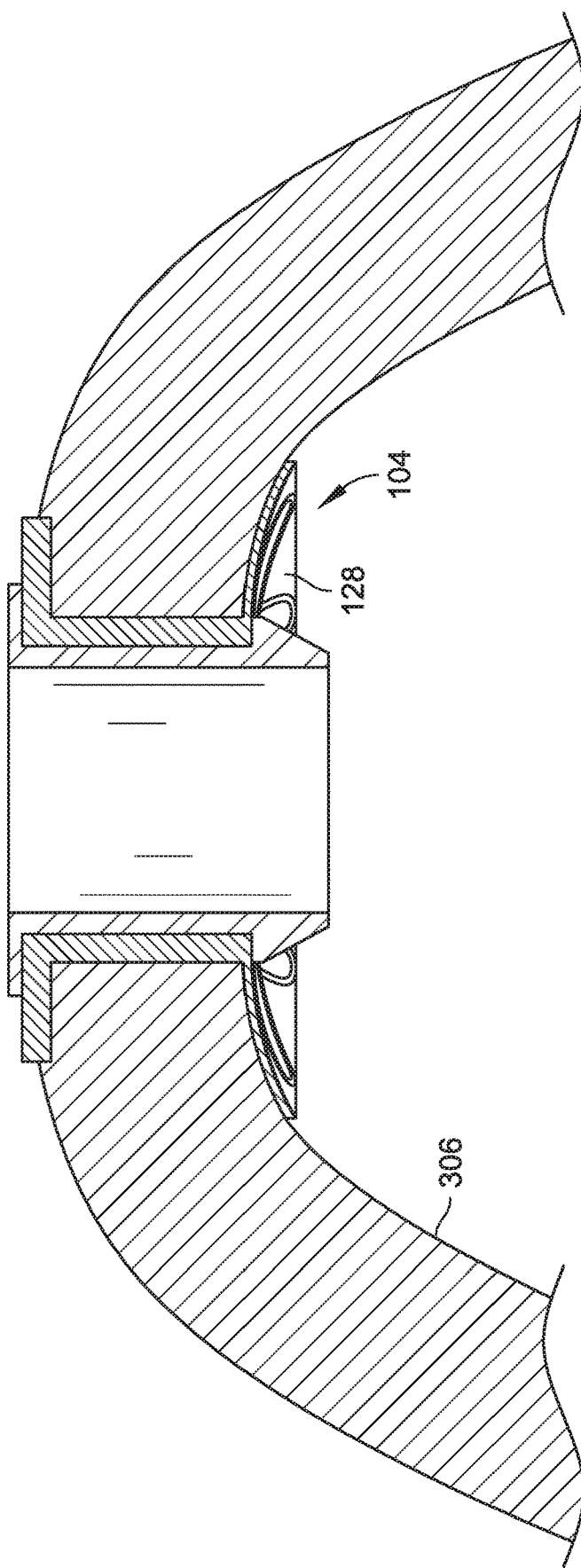
FIG. 3F is a partial cross-sectional view of the biologic tissue interface device of FIG. 3C inserted into the opening in the heart wall with the deployable portion in the deployed configuration.

The deployable portion 104 is configured to transition between a first configuration (e.g., a collapsed or retained configuration shown in FIGS. 1A, 1C, 2A, 3C, 3E) and a second configuration (e.g., a deployed configuration shown in FIGS. 1B, 1D, 1E, 1F, 2B, 3F) to retain the device 100 in place in the second configuration with respect to biologic tissue by retaining the biologic tissue between the flange 116 and the deployable portion 104 when deployed in the second configuration (e.g., as shown in FIG. 3F). In implementations, the device includes a second deployable portion 104 as an alternative or an addition to the flange 116. For example, referring to FIGS. 1E and 1F, the device 100 includes a first deployable portion 104 (shown as 104A) adjacent the first end 110 of the core 106 and a second deployable portion 104 (shown as 104B) adjacent the second end 112 of the core 106. When each deployable portion 104 is in the second configuration, the device 100 can be held in place by retaining the biologic tissue between the respective deployable portions 104.

In implementations, the deployable portion 104, or portions thereof, is formed from a self-expanding smart material to transition the deployable portion 104 between the first configuration and the second configuration in response to a stimulus (e.g., temperature, electric signal, presence of a chemical, or the like), in response to release from a holding device or tool, or combinations thereof. For example, the deployable portion 104 can include a self-expanding smart material including, but not limited to, nitinol, stainless steel, cobalt chromium, alloys thereof, or combinations thereof, which can transition between the first configuration and the second configuration in response to temperature changes (e.g., transition from the first configuration to the second configuration through an increase or decrease in the temperature of the ambient environment of the device 100, such as following insertion into a biologic tissue) or other stimulus or in response to release from a tool which holds the deployable portion 104 in the retained position during insertion into the biologic tissue. For instance, a placement tool or other device can be used to insert the device 100 into an opening in the biologic tissue (e.g., shown in FIG. 3A), where the placement tool retains the deployable portion 104 in the retained position during insertion. Following insertion or during the insertion process, the tool can release the deployable portion 104, allowing the deployable portion to spring outwards from the retained position or otherwise transition to the deployed configuration (e.g., through the internal force(s) of the material forming the deployable portion 104).

Figure 1B:
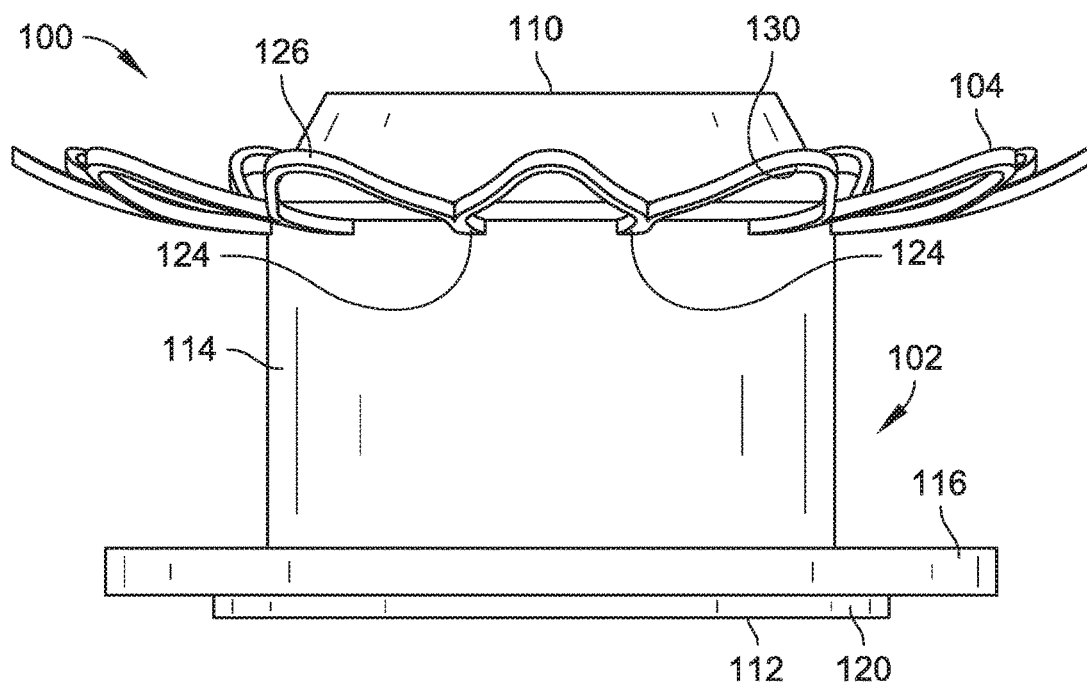
FIG. 1B is a side view of the biologic tissue interface device of FIG. 1A in a deployed configuration.
Figure 1C:
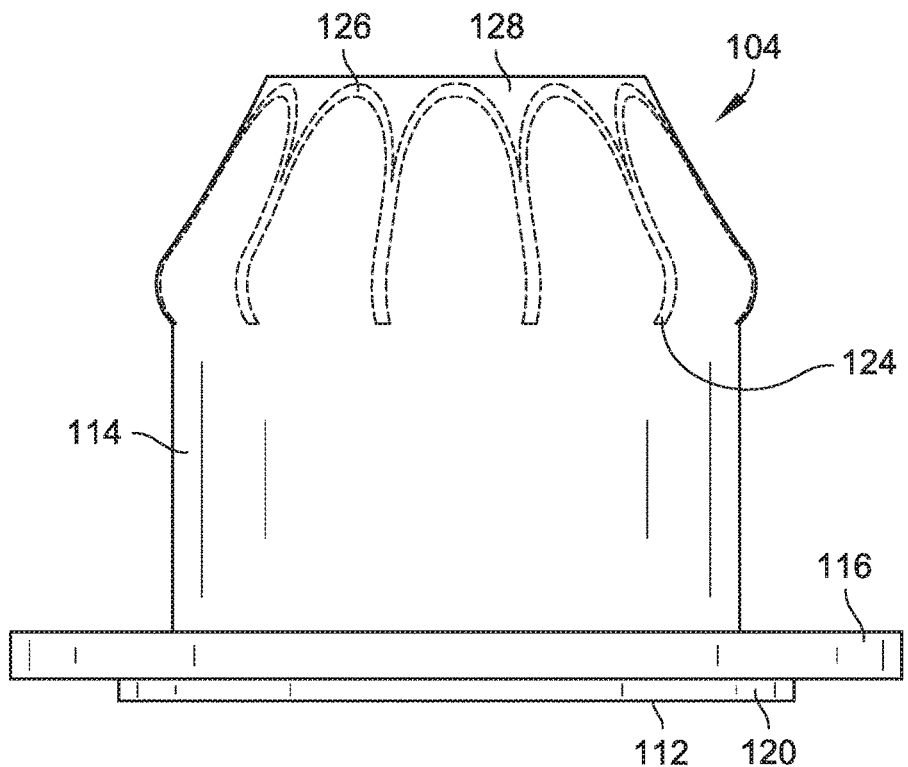
FIG. 1C is a side view of a biologic tissue interface device having fibrous material on a deployable portion in accordance with example implementations of the present disclosure.
Figure 1D:
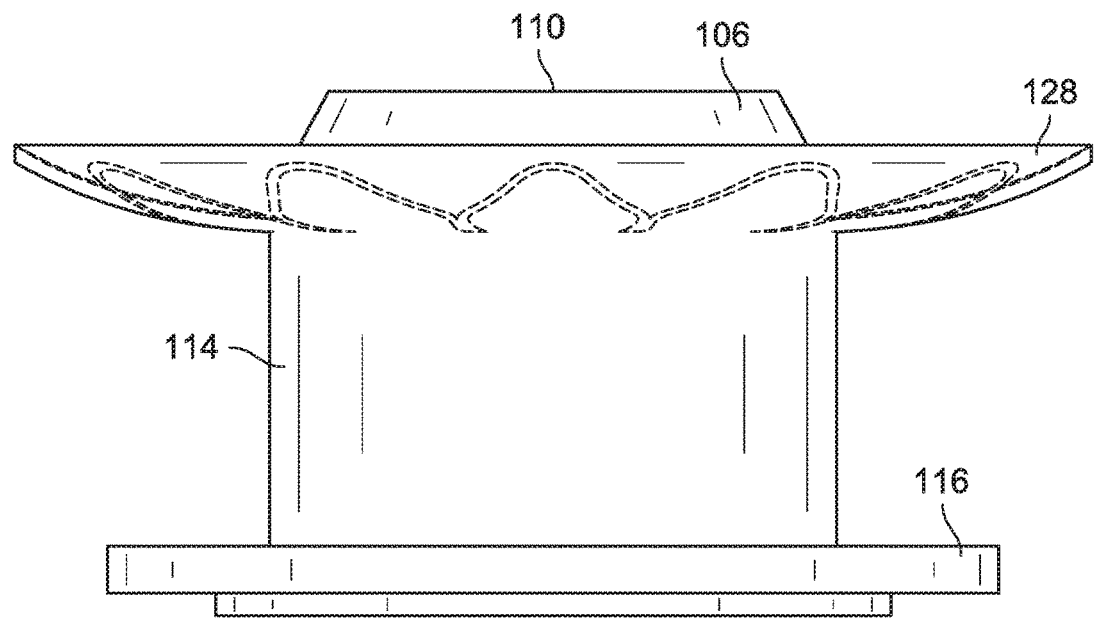
FIG. 1D is a side view of the biologic tissue interface device of FIG. 1C in a deployed configuration.
Figure 1E:
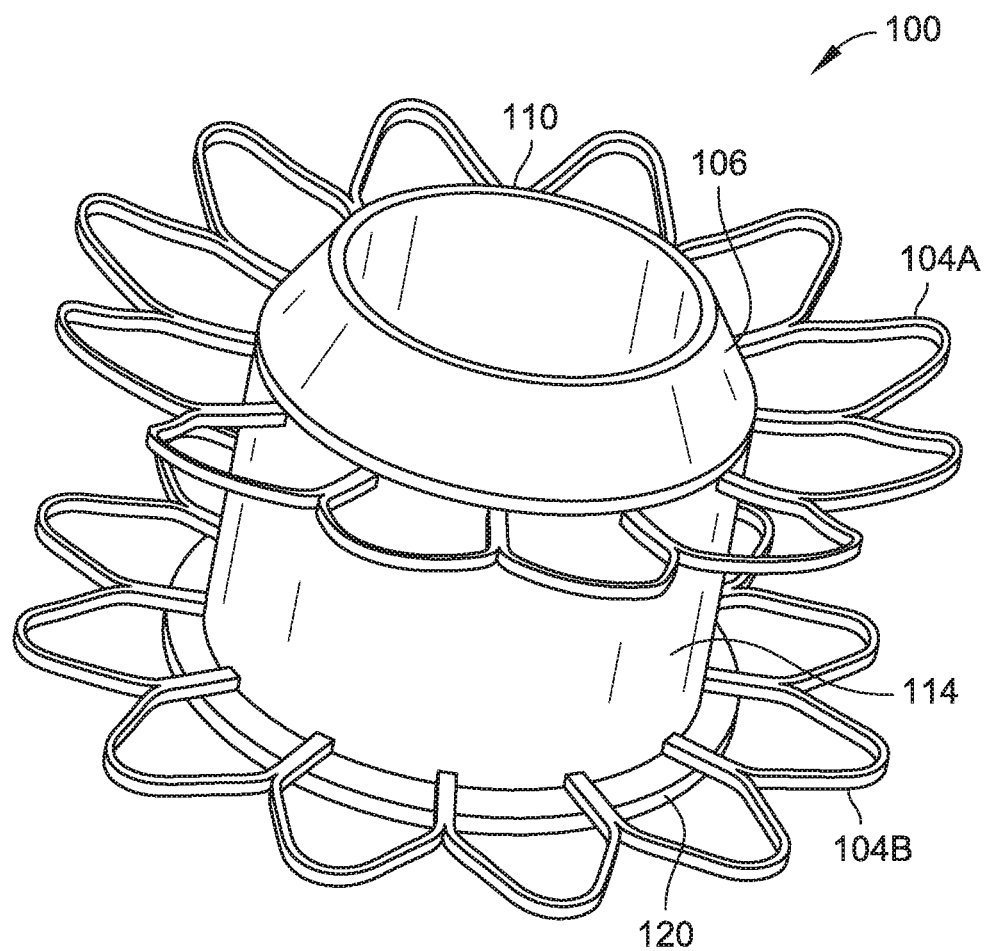
FIG. 1E is an isometric view of a biologic tissue interface device having first and second deployable portions in a deployed configuration in accordance with example implementations of the present disclosure.
Figure 1F:
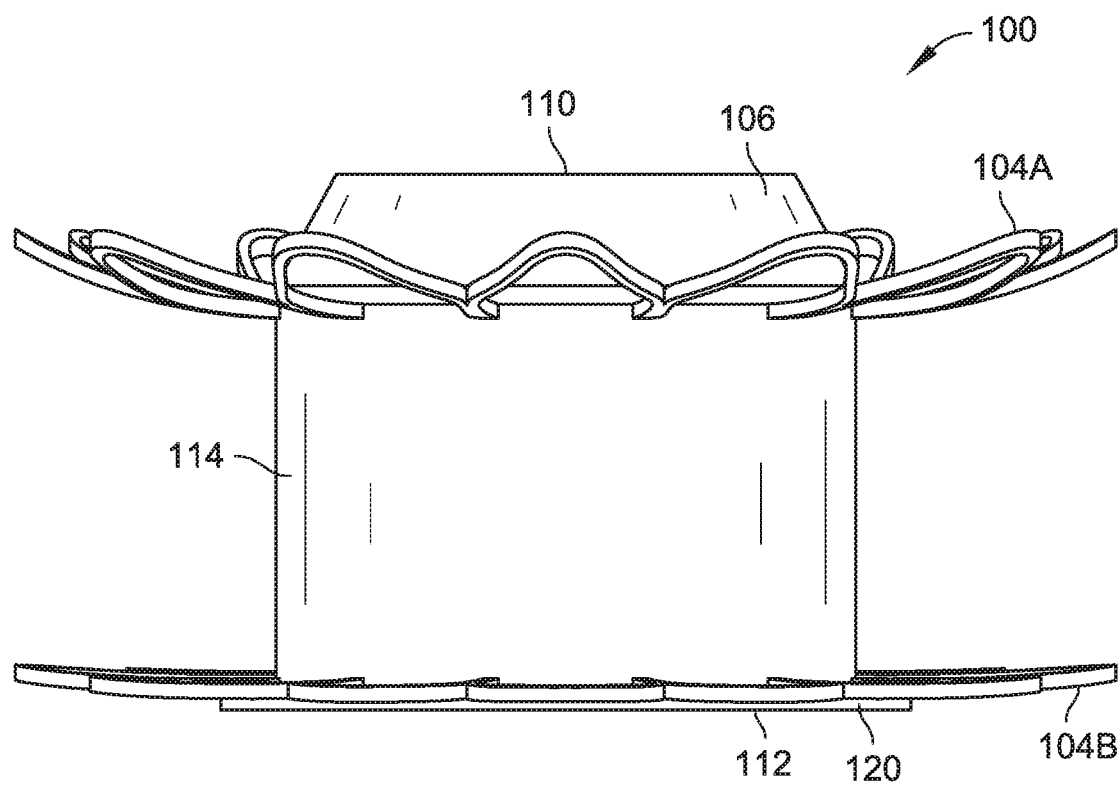
FIG. 1F is a side view of the biologic tissue interface device of FIG. 1E.
Figure 2A:
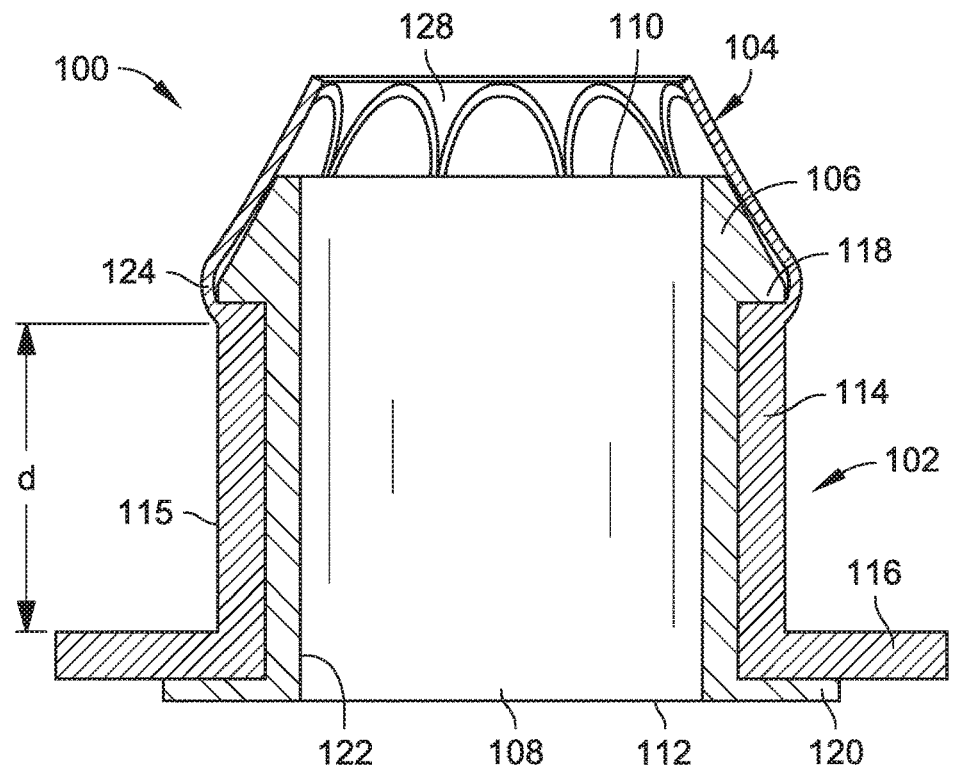
FIG. 2A is a cross-sectional view of the biologic tissue interface device of FIG. 1C in a retained configuration.
Figure 2B:
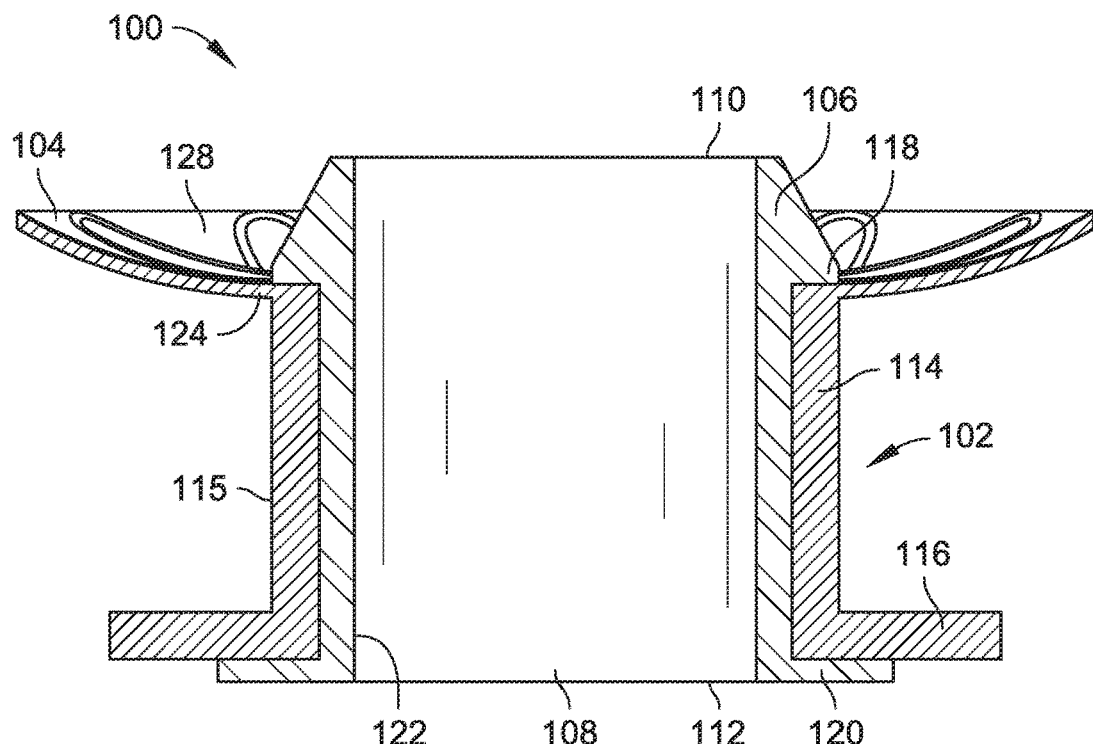
FIG. 2B is a cross-sectional view of the biologic tissue interface device of FIG. 1C in a deployed configuration.

The deployable portion 104 is shown coupled to the sleeve 114 (e.g., affixed to an outer surface of the sleeve 114, welded to the sleeve 114, or otherwise attached to the sleeve 114), however the deployable portion 104 alternatively or additionally could be attached to a portion of the core 106. In implementations, the deployable portion 104 includes a wired structure which at least partially cantilevers from the body portion 102 when in the second configuration, to provide a flange-like geometry to support the device 100 relative to the biologic tissue (e.g., as shown in FIG. 3F). For example, the deployable structure 104 can include, but is not limited to, a scalloped wire configuration (e.g., as shown in FIGS. 1A-1C) having end points 124 coupled to the body portion 102, where a top portion 126 of the scalloped wire distal the end points 124 extends away from the body portion 102 in the second configuration to provide a flange-like structure to retain the biologic tissue between the deployable portion 104 and the flange 116. In implementations, the top portion 126 extends beyond the first end 110 of the core 106 in a longitudinal direction (e.g., from the first end 110 to the second end 112) when the deployable portion 104 is in the first configuration, whereas the first end 110 of the core 106 extends beyond the top portion 126 when the deployable portion 104 is in the second configuration, such as to provide a gap between the native biologic tissue and the first end 110 of the core 106 and the channel 108 formed therein when the deployable portion 104 is in the second configuration. Such gap can retain the biologic material a suitable distance away from the channel 108 (or opening thereof) of the device 100 to prevent occlusion of the channel 108 by the biologic tissue, which in turn could cause dangerous blockages or restrictions in access between the internal biologic tissue and the environment external to the internal biologic tissue (e.g., between an interior environment of the heart and an environment external the heart).

The deployable portion 104 is configured to support stable ingrowth with the native tissue. In implementations, the wired structure of the deployable portion 104 is coated with a fibrous material (e.g., woven or bonded materials) to support the ingrowth of tissue and formation of stable neointima. For example, the deployable portion 104 can include materials including, but not limited to, a polytetrafluoroethylene (PTFE) felt, polyethylene terephthalate (PET), bovine pericardium, or the like, or combinations thereof. Referring to FIGS. 1D, 2A, 2B, 3E, and 3F, the deployable portion 104 includes a fibrous material 128 supported by the wired structure. For example, the fibrous material 128 can be coupled to an outer surface 130 (shown in FIGS. 1A and 1B) of the wired structure that is distal from the body portion 102, such that when the deployable portion 104 is in the second configuration, the fibrous material 128 is adjacent to the biologic material (e.g., as shown in FIG. 3F). Alternatively or additionally, the fibrous material 128 can be positioned on an interior surface of the wired structure of the deployable portion 104, such as to cover or enclose the deployable portion 104. The deployable portion 104 can therefore retain the biologic material a safe distance away from the channel 108 (or opening thereof) of the device 100 to prevent occlusion. In implementations, the first end 112 of the device 100 can include, additionally or alternatively to the flange 116, a self-expanding deployable portion 104B forming a flange-like structure when in a deployed configuration. The self-expanding portion can include one or more of nitinol, stainless steel, cobalt chromium, alloys thereof, or combinations thereof, a polytetrafluoroethylene (PTFE) felt, polyethylene terephthalate (PET), bovine pericardium, or the like, or combinations thereof, where the a fibrous structure can be added to the deployable portion 104B to facilitate biologic tissue ingrowth and aid in hemostasis at the first end 112.

Referring to FIGS. 3A through 3F, the device 100 is shown being inserted within a heart wall 300, however the device 100 is not limited to such application, and can be utilized with other tissue or organs. Referring to FIG. 3B, an opening 302 is made within the heart wall 300. The opening can be made through any appropriate method, including, but not limited to, cutting and removing tissue, dilating or expanding tissue, cruciate incision, or the like. Referring to FIG. 3C, the device 100 is shown prepared for insertion into the opening 302, with the deployable portion 104 in the first configuration (e.g., with the wire structure in a collapsed or retained configuration), and with the first end 110 positioned towards the opening 302. In implementations, a placement tool is utilized to maintain the deployable portion 104 in the retained position, to direct the device 100 into the opening 302, or combinations thereof. Referring to FIGS. 3D and 3E, the device 100 is in position within the opening 302 with the deployable portion 104 still in the first configuration. When the device 100 is in position within the opening 302, the flange 116 is positioned against or adjacent a first surface 304 of the tissue of the heart wall 300 (e.g., an epicardial region), and the sleeve 114 is supported against the heart wall 300 to provide hemostasis.

Referring to FIG. 3F, the device 100 is in position within the opening 302 with the deployable portion 104 having transitioned from the first configuration to the second configuration. Such transition can be facilitated, for example, by a change in temperature of the deployable portion 104, where the deployable portion 104 begins in the first configuration at a first temperature and transitions to the second configuration upon exposure to a second temperature (e.g., warmed by the body of the individual subject), by internal forces of the deployable portion 104 upon release by the placement tool, or combinations thereof. In implementations, tooling can be used to retain the deployable portion 104 in the first configuration to prevent expansion of the deployable portion 104 at the time of temperature transition until a time at which the tooling permits the deployable portion 104 to deploy. For example, the placement tool can physically hold the deployable portion 104 in the first configuration during positioning of the device 100 within the opening 302, where subsequent release of the deployable portion 104 by the placement tool permits the transition from the first configuration to the second configuration (e.g., through exposure to temperature transitions, through permitting the internal forces of the deployable portion 104 to spring outwards, or combinations thereof). As shown, in the second configuration, the deployable portion 104 is positioned against or adjacent a second surface 306 of the tissue of the heart wall 300 (e.g., an endocardial region). In implementations, the device 100 defines a distance d (shown in FIG. 2A) between a surface of the flange 116 to be positioned against the biologic tissue and the end points 124 of the wired structure of the deployable portion 104, where the distance d is configured based on an expected width of tissue that defines the opening 302. By incorporating a flange or flange-like device on both surfaces 304 and 306, the device 100 can facilitate variations in wall thickness of the heart wall 300 or other biologic tissue with a single device 100. For instance, the flexible nature of the deployable portion 104 can provide retention against the second surface 306 at varying thicknesses of the heart wall 300 with respect to the positioning of the flange 116 or secondary deployable portion (e.g., deployable portion 104B).

Figure 4A:
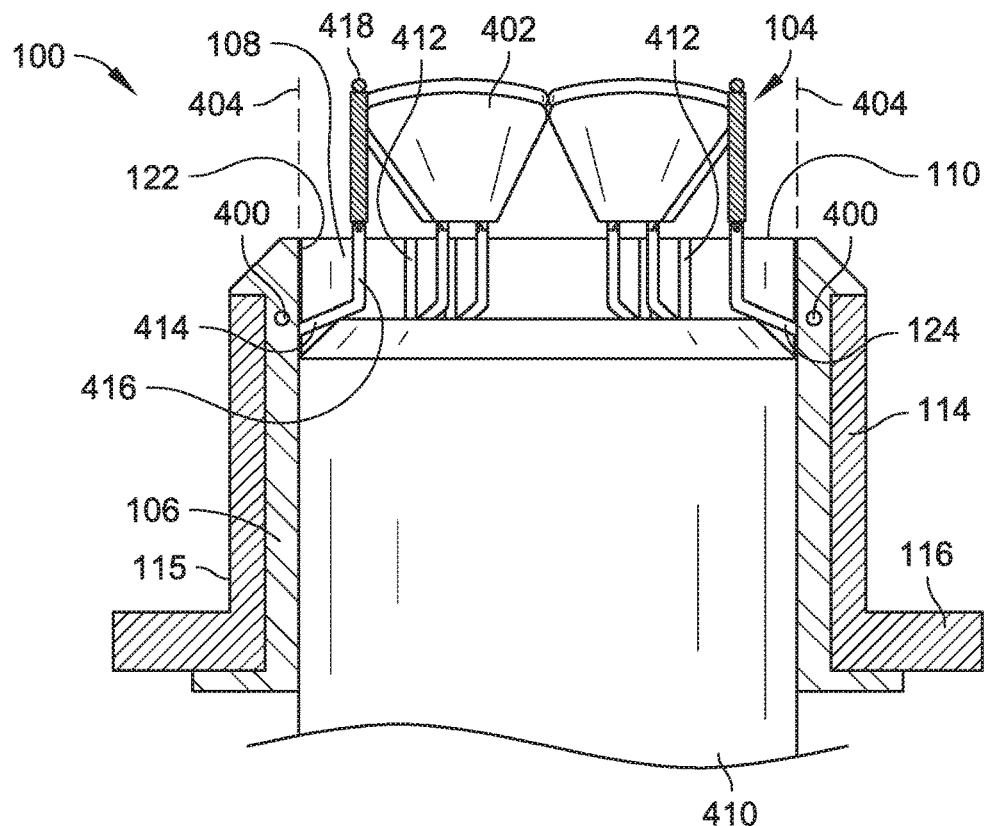
FIG. 4A is a partial cross-sectional view of a biologic tissue interface device in accordance with example implementations of the present disclosure.
Figure 4B:
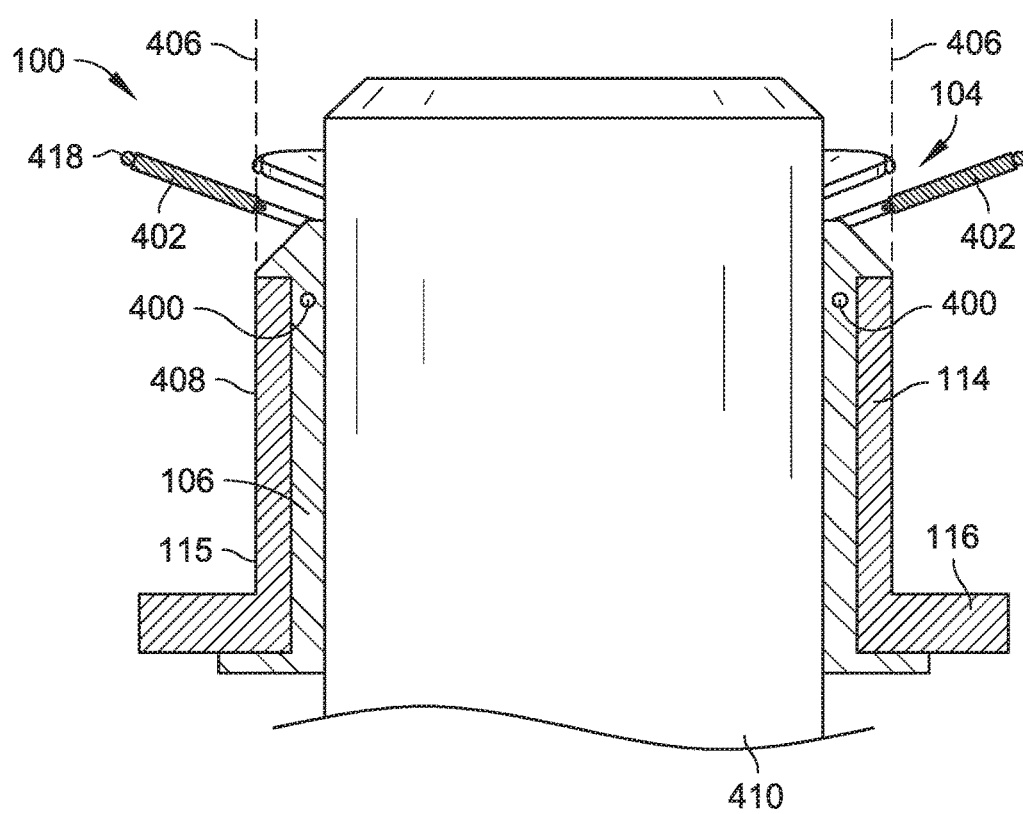
FIG. 4B is a partial cross-sectional view of the biologic tissue interface device of FIG. 4A being transitioned to a deployed configuration with another object.

Referring to FIGS. 4A and 4B, the device 100 is shown with an interior attachment of the deployable portion 104 with respect to the body portion 102. The end points 124 of the wired structure of the deployable portion 104 are coupled to the core 106 adjacent the first end 110 by a rotatable connector 400. In the retained configuration (shown in FIG. 4A), the wired structure extends inwardly from the rotatable connector on the core 106 towards the channel 108, and then extends vertically out from the channel past the first end 110. The wired structure can include, but is not limited to, one or more fan structures 402 which transition from a location confined by a vertical perimeter 404 of the inner surface 122 of the core 106 when in the retained configuration to a location extending beyond a vertical perimeter 406 of an outer surface 408 of the sleeve 114 when in the deployed configuration (shown in FIG. 4B). For example, an end portion 418 of the deployable portion 104 is held within the vertical perimeter 404 when the deployable portion 104 is in the retained configuration, and the end portion 418 extends beyond the vertical perimeter 406 in a direction from the channel 108 to the exterior surface 115 of the body portion 102 when the deployable portion 104 is in the deployed configuration. In implementations, the device 100 is transitioned between the retained configuration and the deployed configuration through use of a ram 410 or other object which physically contacts the deployable portion 104 to rotate the end points 124 of the wired structure about the rotatable connector 400 to push the fan structures 402 outward (e.g., through the vertical perimeter 406). The fan structures 402 are then positioned to promote biologic tissue ingrowth and formation of stable neointima while retaining the biologic material a safe distance away from the channel 108 (or opening thereof) of the device 100 to prevent occlusion.

In implementations, the core 106 defines one or more channels 412 into which at least a portion of the wired structure of the deployable portion 104 can enter when transitioned between the retained configuration and the deployed configuration. For example, the wired structure of the deployable portion 104 can include a first portion 414 coupled to the rotatable connector 400 and extended inwardly into the channel 108 when the deployable portion 104 is in the retained configuration and a second portion 416 coupled to the first portion 414 and extended out from the channel 108 terminating at the fan structure 402. The first portion 414 can interface with the channel 412 in the core 106 during transition between the retained configuration and the deployed configuration, such as to pass substantially into the channel 412 to position the first portion 414 substantially vertically and to position the second portion 416 extending outwardly from the body portion 102 to place the fan structures 402 in the deployed configuration. Additionally or alternatively to assisted deployment by the ram 410, the deployable portion 104 having the fan structures 402 can be held in the retained configuration by a placement tool during insertion of the device 100 into the biologic tissue to prevent expansion of the deployable portion 104 until a time at which the tooling permits the deployable portion 104 to deploy. For example, the placement tool can physically hold the deployable portion 104 in the retained configuration during positioning of the device 100 within the biologic tissue, where subsequent release of the deployable portion 104 by the placement tool permits the transition from the retained configuration (shown in FIG. 4A) to the deployed configuration (shown in FIG. 4B), where the transition is facilitated by exposure to temperature transitions, by allowing the internal forces of the deployable portion 104 to spring outwards, or combinations thereof.

Figure 5A:
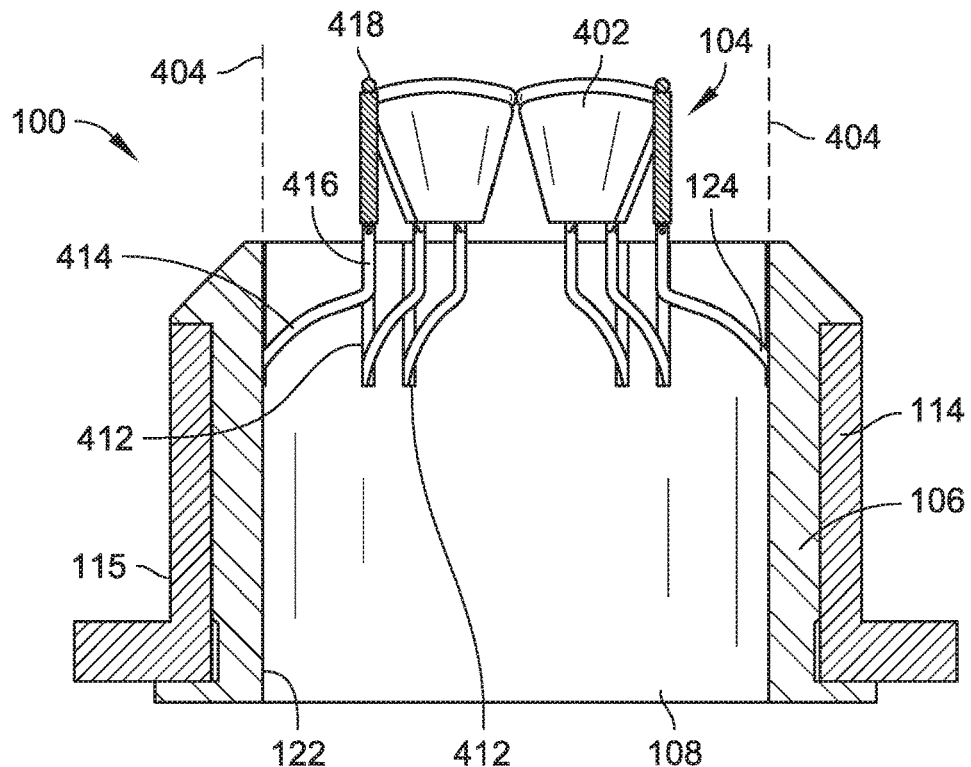
FIG. 5A is a partial cross-sectional view of a biologic tissue interface device in accordance with example implementations of the present disclosure.
Figure 5B:
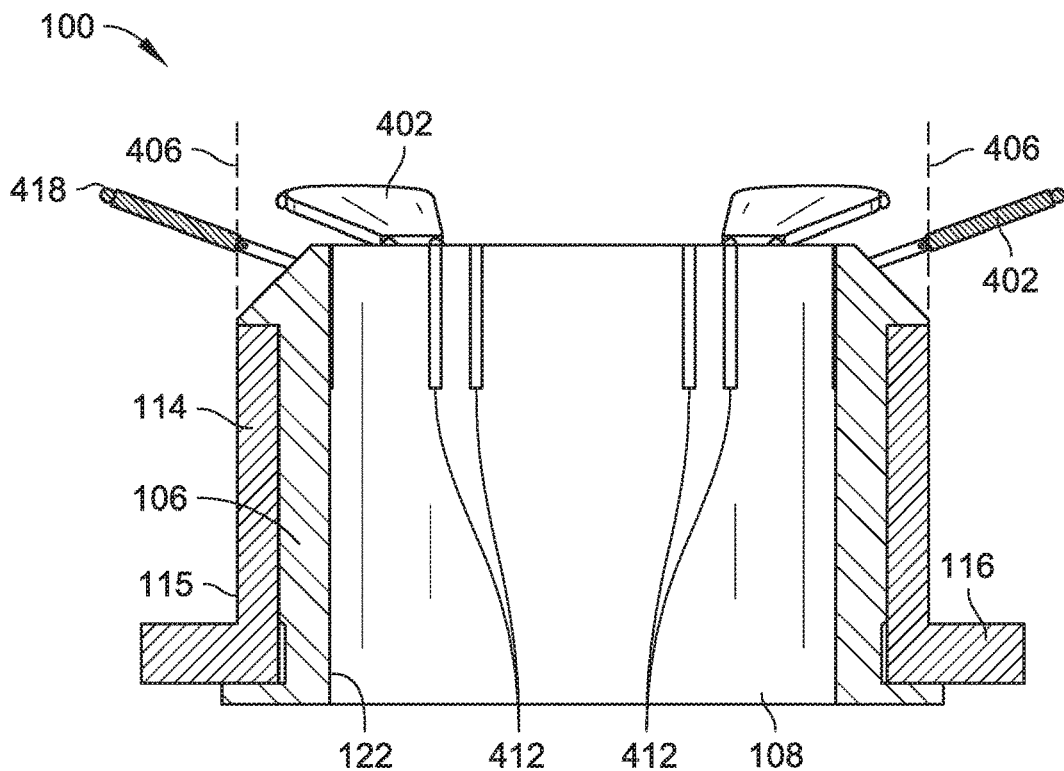
FIG. 5B is a partial cross-sectional view of the biologic tissue interface device of FIG. 5A in a deployed configuration in accordance with example implementations of the present disclosure.

Referring to FIGS. 5A and 5B, the device 100 is shown with an interior attachment of the deployable portion 104 in accordance with an implementation. The ends points 124 of the wired structure of the deployable portion 104 are coupled to the inner surface 122 of the core 106. For instance, at least a portion of the wired structure is cantilevered toward an interior of the channel 108 when in the retained configuration (shown in FIG. 5A). The deployable portion 104 can be formed from a self-expanding material including, but not limited to, nitinol, stainless steel, cobalt chromium, alloys thereof, or combinations thereof, where the self-expanding material transitions the deployable portion between the retained configuration (shown in FIG. 5A) and the deployed configuration (shown in FIG. 5B) upon exposure to a stimulus (e.g., temperature, electric signal, presence of a chemical, or the like), through internal forces of the deployable portion 104 causing the deployable portion 104 to spring outwards upon release by the placement tool, or combinations thereof. The wired structure can include, but is not limited to, one or more fan structures 402 which transition from a location confined by the vertical perimeter 404 of the inner surface 122 of the core 106 when in the retained configuration to a location extending beyond the vertical perimeter 406 of the outer surface 408 of the sleeve 114 when in the deployed configuration (shown in FIG. 5B). For example, the end portion 418 of the deployable portion 104 is held within the vertical perimeter 404 when the deployable portion 104 is in the retained configuration, and the end portion 418 extends beyond the vertical perimeter 406 in a direction from the channel 108 to the exterior surface 115 of the body portion 102 when the deployable portion 104 is in the deployed configuration. The core 106 can define one or more channels 412 into which at least a portion of the wired structure of the deployable portion 104 can enter when transitioned between the retained configuration and the deployed configuration. For example, the wired structure of the deployable portion 104 can include a first portion 414 coupled to the inner surface 122 of the core 108 and extended inwardly into the channel 108 when the deployable portion 104 is in the retained configuration and a second portion 416 coupled to the first portion 414 and extended out from the channel 108 terminating at the fan structure 402. The first portion 414 can interface with the channel 412 in the core 106 during transition between the retained configuration and the deployed configuration, such as to pass substantially into the channel 412 to position the first portion 414 substantially vertically and to position the second portion 416 extending outwardly from the body portion 102 to place the fan structures 402 in the deployed configuration. Additionally or alternatively, the ram 410 or other object can be used to facilitate or assist with the transition through physically contact between the ram 410 or other object and the the deployable portion 104 to push the wired structure into the channels 412 to push the fan structures 402 outward (e.g., through the vertical perimeter 406). When the deployable portion 102 is in the deployed position, the fan structures 402 are then positioned to promote biologic tissue ingrowth and formation of stable neointima while retaining the biologic material a safe distance away from the channel 108 (or opening thereof) of the device 100 to prevent occlusion.

Figure 6B:
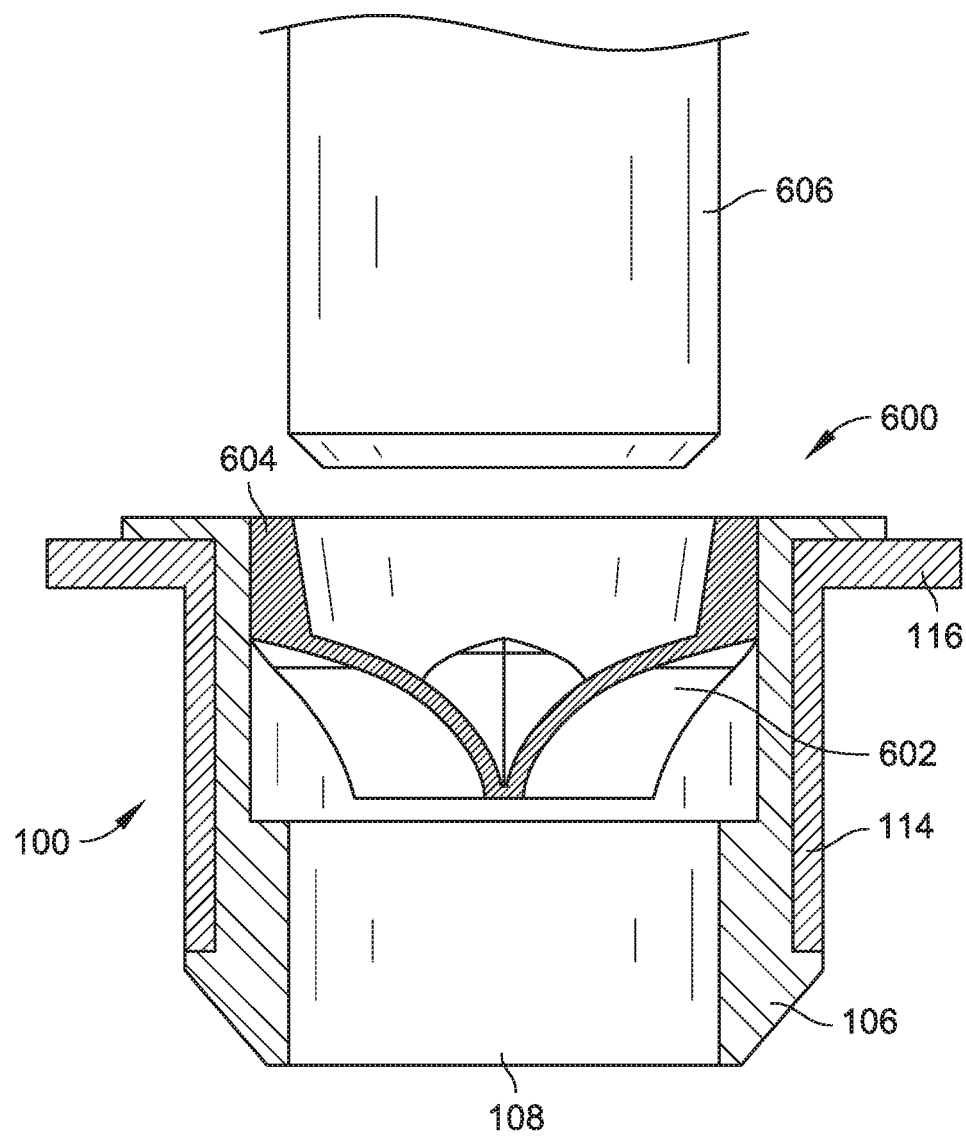
FIG. 6B is a cross-sectional view of the hemostatic valve seal of FIG. 6A positioned in a hemostatic interface device in an undeployed configuration.
Figure 6C:
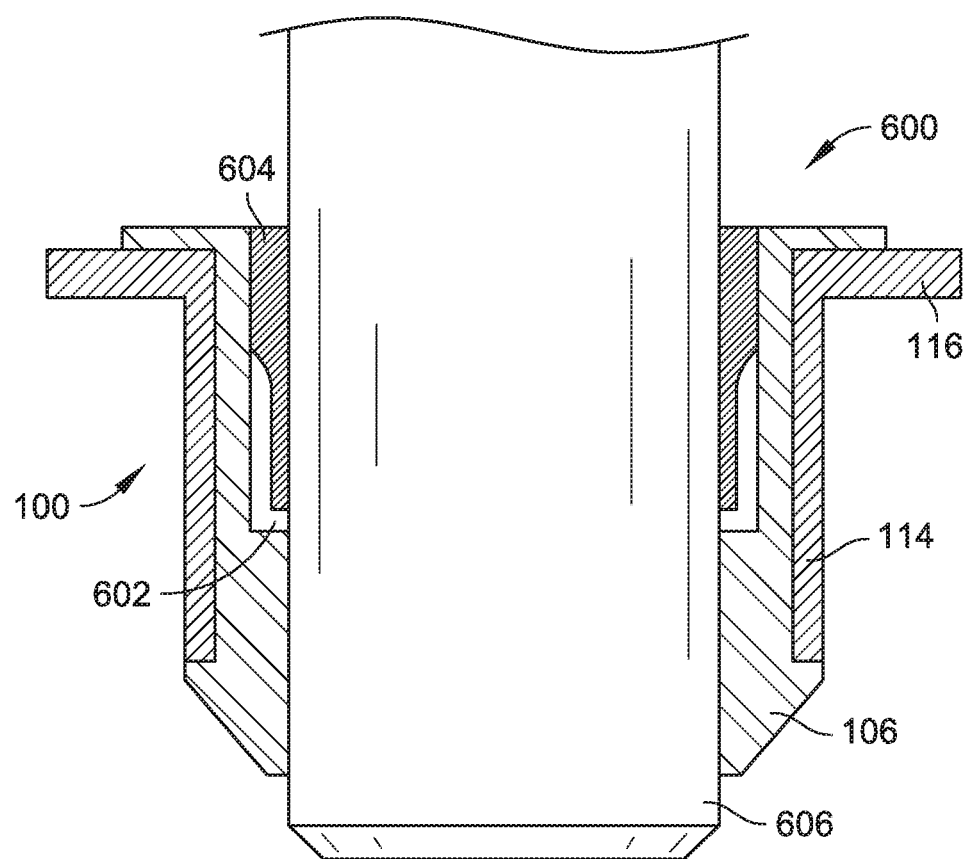
FIG. 6C is a cross-sectional view of the hemostatic valve seal of FIG. 6A positioned in a hemostatic interface device in a deployed configuration.

Referring to FIGS. 6A through 6C, a hemostatic valve seal 600 is shown. The hemostatic valve seal 600 is configured for placement into at least a portion of the channel 108 to provide a barrier to fluid flow when in a retained configuration (shown in FIGS. 6A and 6B). The hemostatic valve seal 600 includes a plurality of flexible members 602 coupled to a valve body 604. The flexible members 602 cover an aperture formed in the valve body 604 when in the retained configuration, and permit access to the aperture when in a deployed configuration (shown in FIG. 6C). In implementations, the flexible members 602 are transitioned from the retained configuration to the deployed configuration through physical contact with an object 606, which can include, for example, a conduit, a portion of a pump, or the like, to permit fluid flow through the hemostatic valve seal 600. For instance, the object 606 can include an interior channel to facilitate fluid flow while the object 606 is placed through the hemostatic valve seal 600 in the channel 108. In implementations, the hemostatic valve seal 600 is introduced to the device 100 during deployment or following deployment of the device 100 into an opening in biologic tissue to prevent the flow of biological fluid (e.g., blood) through the device 100 until the object 606 is to be introduced.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A biologic tissue interface device comprising:
   a body structure including a core and a sleeve disposed around at least a portion of the core, the core defining a channel through the core extending from a first end of the core to a second end of the core, the sleeve including a flange adjacent the second end of the core; and
   a deployable portion coupled to the body structure adjacent the first end of the core, the deployable portion having a wired structure transitionable between a retained configuration and a deployed configuration, wherein a top portion of the wired structure extends beyond the first end of the core in a longitudinal direction from the second end of the core to the first end of the core when the wired structure is in the retained configuration, and wherein the first end of the core extends beyond the top portion of the wired structure when the wired structure is in the deployed configuration.

2. The biologic tissue interface device of claim 1, wherein the wired structure is formed from at least one of nitinol, stainless steel, cobalt chromium, or alloys thereof.

3. The biologic tissue interface device of claim 1, wherein an end point of the wired structure of the deployable portion is coupled to an exterior surface of the sleeve.

4. The biologic tissue interface device of claim 1, wherein an end point of the wired structure of the deployable portion is coupled to an interior surface of the core, the interior surface defining the channel.

5. The biologic tissue interface device of claim 4, wherein the core defines a plurality of channels into which at least a portion of the wired structure fits when the wired structure is in the deployed configuration.

6. The biologic tissue interface device of claim 4, wherein the end point of the wired structure is coupled to the interior surface of the core via a rotatable connector about which the wired structure rotates during transition between the retained configuration and the deployed configuration.

7. The biologic tissue interface device of claim 1, wherein the core includes a first flange adjacent the first end and a second flange adjacent the second end, and wherein the sleeve is coupled between the first flange and the second flange.

8. The biologic tissue interface device of claim 1, wherein the sleeve includes a fibrous material.

9. The biologic tissue interface device of claim 1, wherein the sleeve includes at least one of a polytetrafluoroethylene (PTFE) felt, polyethylene terephthalate (PET), or bovine pericardium.

10. The biologic tissue interface device of claim 1, wherein the deployable portion includes a fibrous material coupled to the wired structure.

11. The biologic tissue interface device of claim 1, wherein the deployable portion includes at least one of a polytetrafluoroethylene (PTFE) felt, polyethylene terephthalate (PET), or bovine pericardium coupled to the wired structure.

12. The biologic tissue interface device of claim 1, further including a hemostatic valve seal coupled to the core and covering the channel with a plurality of flexible members.

13. The biologic tissue interface device of claim 1, further including a second deployable portion coupled to the core adjacent the second end of the core.

14. A biologic tissue interface device comprising:
   a body structure including a core and a sleeve disposed around at least a portion of the core, the core defining a channel through the core extending from a first end of the core to a second end of the core, the body structure defining a first vertical perimeter extending longitudinally from an interior surface of the core in a direction from the second end of the core to the first end of the core and a second vertical perimeter extending longitudinally from an exterior surface of the body portion in a direction from the second end of the core to the first end of the core, the sleeve including a flange adjacent the second end of the core; and
   a deployable portion coupled to the body structure adjacent the first end of the core, the deployable portion having a wired structure transitionable between a retained configuration and a deployed configuration, wherein an end portion of the deployable portion is held within the first vertical perimeter when the wired structure is in the retained configuration, and wherein the end portion of the deployable portion extends beyond the second vertical perimeter in a direction from the channel to the exterior surface of the body portion when the wired structure is in the deployed configuration.

15. The biologic tissue interface device of claim 14, wherein the wired structure is formed from at least one of nitinol, stainless steel, cobalt chromium, or alloys thereof.

16. The biologic tissue interface device of claim 14, wherein an end point of the wired structure of the deployable portion is coupled to the exterior surface of the body portion.

17. The biologic tissue interface device of claim 14, wherein an end point of the wired structure of the deployable portion is coupled to an interior surface of the core, the interior surface defining the channel.

18. The biologic tissue interface device of claim 17, wherein the core defines a plurality of channels into which at least a portion of the wired structure fits when the wired structure is in the deployed configuration.

19. The biologic tissue interface device of claim 14, wherein the core includes a first flange adjacent the first end and a second flange adjacent the second end, and wherein the sleeve is coupled between the first flange and the second flange.

20. The biologic tissue interface device of claim 14, wherein at least one of the sleeve and the deployable portion includes a fibrous material.

* * * * *